(12) United States Patent
Ma

(10) Patent No.: US 9,186,077 B2
(45) Date of Patent: Nov. 17, 2015

(54) METHOD AND DEVICE WITH CUSTOMIZABLE POWER MANAGEMENT

(75) Inventor: Jeong J. Ma, Long Grove, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 946 days.

(21) Appl. No.: 13/398,099

(22) Filed: Feb. 16, 2012

(65) Prior Publication Data

US 2013/0217978 A1    Aug. 22, 2013

(51) Int. Cl.
   *A61B 5/00* (2006.01)
   *A61B 5/024* (2006.01)
   *A61B 5/11* (2006.01)

(52) U.S. Cl.
   CPC ........... *A61B 5/02438* (2013.01); *A61B 5/4809* (2013.01); *A61B 5/681* (2013.01); *A61B 5/1118* (2013.01); *A61B 5/6802* (2013.01); *A61B 5/7275* (2013.01); *A61B 2560/0209* (2013.01)

(58) Field of Classification Search
   CPC ........ H04B 13/02; H04B 15/00; G06Q 10/06; G06Q 30/02; G06Q 30/0233; A61B 5/1118; A61B 5/02438; A61B 5/6802; A61B 5/7275; A61B 5/4809; A61B 5/681; A61B 2560/0209
   See application file for complete search history.

(56) References Cited

U.S. PATENT DOCUMENTS

| | | | |
|---|---|---|---|
| 5,924,979 A | 7/1999 | Swedlow et al. | |
| 6,119,040 A * | 9/2000 | Chirife | 607/18 |
| 6,572,511 B1 | 6/2003 | Volpe | |
| 6,608,549 B2 * | 8/2003 | Mynatt et al. | 340/5.8 |
| 2007/0032731 A1 * | 2/2007 | Lovejoy et al. | 600/500 |
| 2007/0093720 A1 | 4/2007 | Fischell et al. | |
| 2007/0203421 A1 | 8/2007 | Cho et al. | |
| 2007/0244398 A1 | 10/2007 | Lo et al. | |
| 2008/0058616 A1 | 3/2008 | Nakagawa et al. | |
| 2009/0281435 A1 | 11/2009 | Ahmed et al. | |
| 2010/0056341 A1 | 3/2010 | Ellis et al. | |
| 2010/0113950 A1 | 5/2010 | Lin et al. | |
| 2011/0092780 A1 | 4/2011 | Zhang et al. | |
| 2011/0207509 A1 | 8/2011 | Crawford | |
| 2012/0203077 A1 | 8/2012 | He et al. | |

OTHER PUBLICATIONS

Patent Cooperation Treaty, International Search Report and Written Opinion of the International Searching Authority for International Application No. PCT/US2013/024824, Jul. 3, 2013, 11 pages.
International Preliminary Report on Patentability from international application No. PCT/US2013/024824, mailed Aug. 28, 2014, 8 pp.

(Continued)

*Primary Examiner* — William Thomson
*Assistant Examiner* — Shirley Jian
(74) *Attorney, Agent, or Firm* — Shumaker & Sieffert, P.A.

(57) ABSTRACT

A wireless communication device (200) and method (300) customizable power management. The method (300) can include: providing (310) a wireless communication device including an energy storage device; sensing (320) heart rate data of a user; and configuring (330) the wireless communication device's functionality based on the sensed heart rate data. Advantageously, the device (200) and method (300) can provide a real-time attribute of a user, which can be used to configure the functionality of a device and conserve power.

16 Claims, 5 Drawing Sheets

(56) References Cited

OTHER PUBLICATIONS

Motoactv, http://www.motorola.com/staticfiles/Support/US-EN/Mobile%20Phones%20Accessories/MOTOACTV/Documents/Staticfiles/MOTOACTV_UG_US_68016649001B.pdf, Motorola, Jun. 29, 2012, all pages.

Laterdroid: JuiceDefender—Battery Saver, https://play.google.com/store/apps/details?id=com.latedroid.juicedefender&feature=related_apps#?t=W251bGwsMSwxLDEwOSwiY29tLmxhdGVkcm9pZC5qdWljZWRlZmVuZGVyII0., Google Play, Jun. 29, 2012, all pages.

* cited by examiner

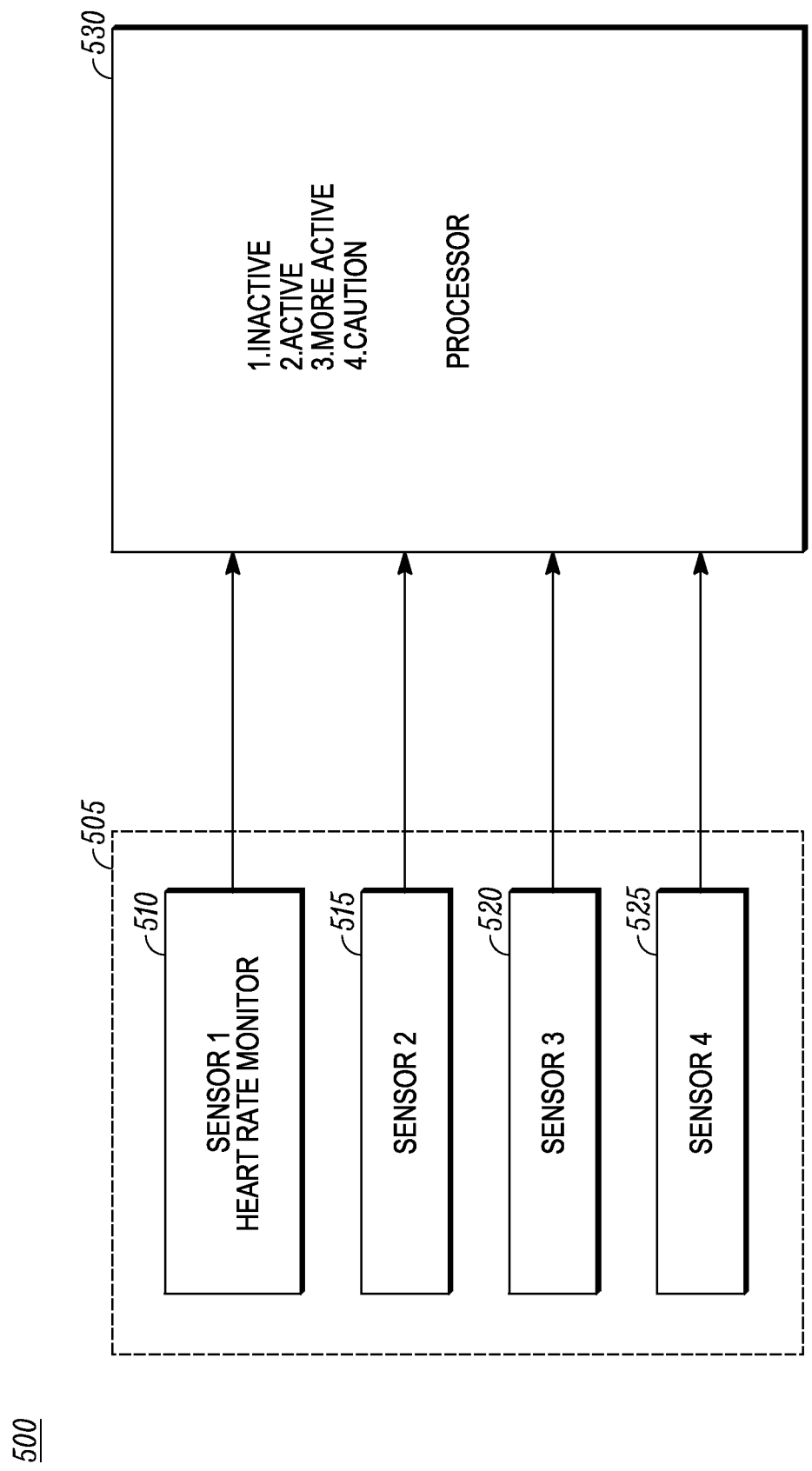

METHOD AND DEVICE WITH CUSTOMIZABLE POWER MANAGEMENT

BACKGROUND

1. Field

The present disclosure relates to a method and device with customizable power management.

2. Introduction

Watch phones have been around for some time and the form factor has not gained much consumer attention. Perhaps that is due to the fact that they are not compelling products, functional and impressive, fail to have highly desirable specifications, applications and functions, and because a user has to hold his or her arm in the air to make a call or use a headset.

However, wearable devices and watch phones do provide use cases, such as minimizing the possibility of leaving ones phone behind, not taking up valuable pocket space, and appearing to be a secret agent when making a call. Wearable devices have excellent use cases, in connection with health, medical and wellness applications requiring twenty four hour connectivity.

There is a need for enabling effective and reliable power management for wireless communication devices, including wearable devices that are smart, portable and can communicate with accessories, such as with sensors configured to monitor users health condition using various technologies or systems, such as a Personal Area Network (PAN), Body Area Network (BAN), Near Field Communication (NFC), BLUETOOTH® or WIFI®, for example.

One of the more important design challenges in wireless communication devices including wearable devices is maximizing battery life and managing power use. Now that "wireless mobility and connectivity" has become a major user expectation, users demand power longevity in such devices. As more and more features, computing power, and memory are packed into wireless communication devices and wearable devices, there is a need for enhanced functionality in such devices, with satisfactory battery life.

There is also need to reduce the amount of power a circuit consumes and techniques to effectively manage the available power using on-device techniques, circuits and sensors.

There is a further need for methods and devices with customizable power management, to better manage power to maintain the usefulness of a device. Thus, there is a need for improving, customizing and managing battery life in electronic devices, such as wireless communication devices, such as cell phones, wearable devices and accessories.

It would be considered an improvement in the art, if a wireless communication method and electronic devices with enhanced power management were developed. There is yet a further need to provide an intelligent method and device adapted to provide personalized and reliable battery management information to a user. Thus, a method and device with intelligent or customized power management that addresses these needs, would be considered an improvement in the art.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which:

FIG. 5 is an exemplary block diagram of a wireless communication customizable power management according to one embodiment, including a power management module, sensor module and processor

DETAILED DESCRIPTION

Figure 1:
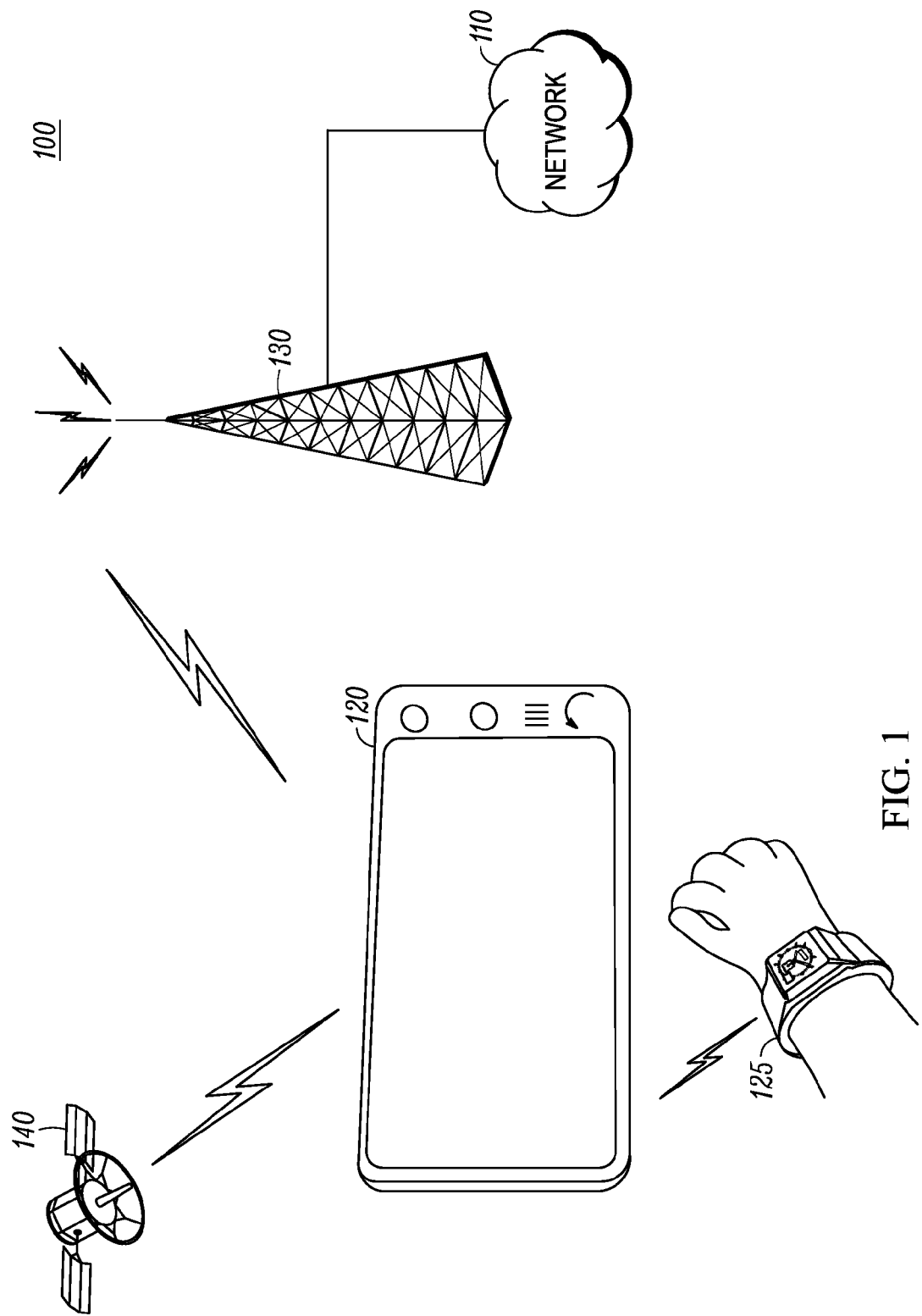
FIG. 1 is an exemplary block diagram of a communication system according to one embodiment.
Figure 2:
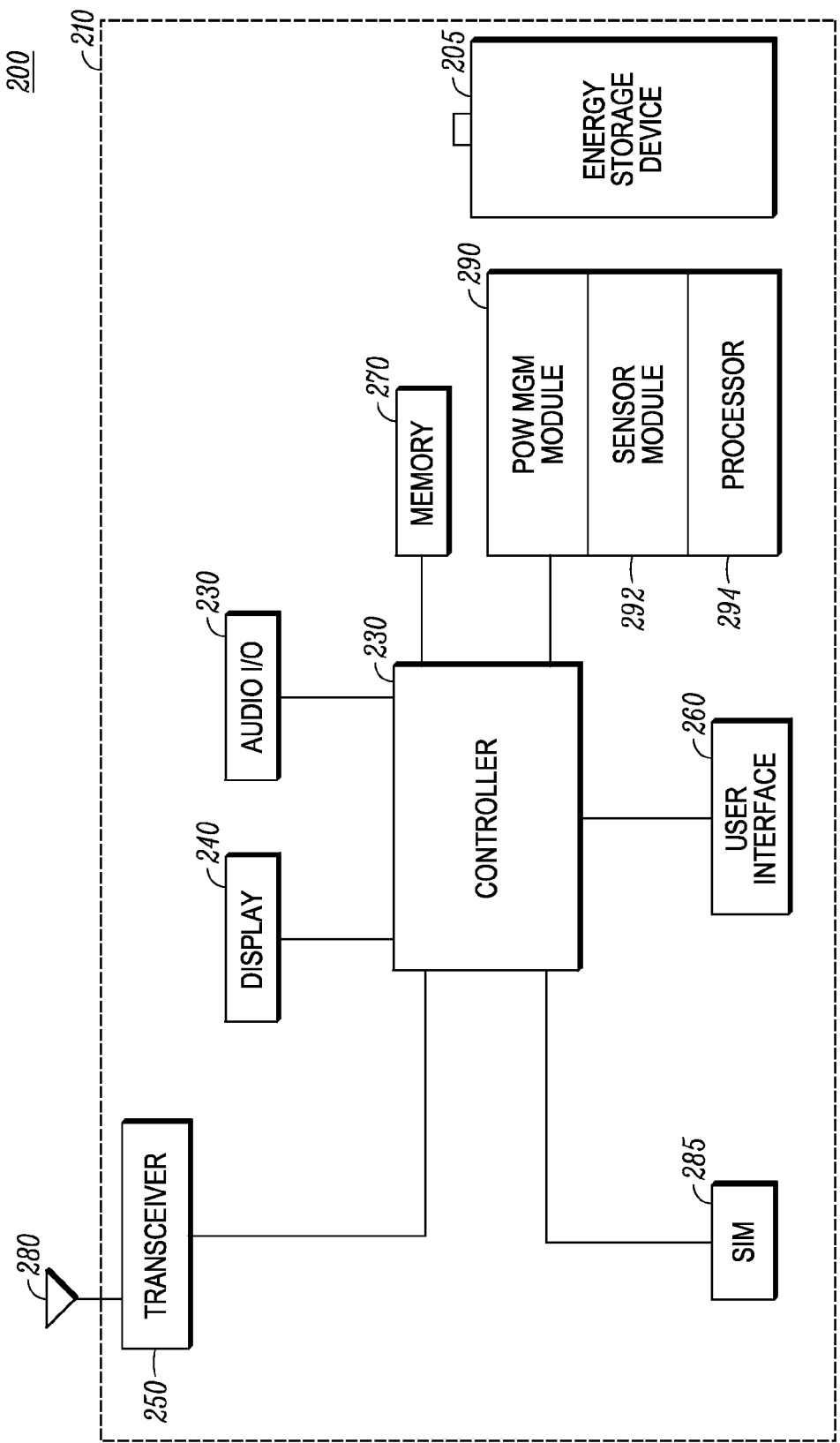
FIG. 2 is an exemplary block diagram of a wireless communication device with customizable power management according to one embodiment.

FIG. 1 is an exemplary block diagram of a system 100 according to one embodiment. The system 100 can include a network 110, a terminal 120, and a base station 130. The terminal 120 may be a wireless communication device, such as a wireless telephone, a wearable device, a cellular telephone, a personal digital assistant, a pager, a personal computer, a tablet, a selective call receiver, or any other device that is capable of sending and receiving communication signals on a network including a wireless network. The network 110 may include any type of network that is capable of sending and receiving signals, such as wireless signals. For example, the network 110 may include a wireless telecommunications network, a cellular telephone network, a Time Division Multiple Access (TDMA) network, a Code Division Multiple Access (CDMA) network, Global System for Mobile Communications (GSM), a Third Generation (3G) network, a Fourth Generation (4G) network, a satellite communications network, and other like communications systems. More generally, network 110 may include a Wide Area Network (WAN), a Local Area Network (LAN) and/or a Personal Area Network (PAN). Furthermore, the network 110 may include more than one network and may include a plurality of different types of networks. Thus, the network 110 may include a plurality of data networks, a plurality of telecommunications networks, a combination of data and telecommunications networks and other like communication systems capable of sending and receiving communication signals. In operation, the terminal 120 can include a wireless communication device and/or a wearable device 125 connected as an accessory or as stand alone devices, which communicate with the network 110 and with other devices on the network 110 by sending and receiving wireless signals via the base station 130, which may also comprise local area, and/or personal area access points, as detailed more fully herein. The terminal 120 is shown being in communication with a global positioning system (GPS) 140 satellite, global navigation satellite system (GNSS) or the like, for position sensing and determination. FIG. 2 is an exemplary block diagram of a wireless communication device 200 configured with an energy storage device, battery or module 205, such as in the terminal 120, for example. The wireless communication device 200 can include a housing 210, a controller 220 coupled to the housing 210, audio input and output circuitry 230 coupled to the housing 210, a display 240 coupled to the housing 210, a transceiver 250 coupled to the housing 210, a user interface 260 coupled to the housing 210, a memory 270 coupled to the housing 210, an antenna 280 coupled to the housing 210 and the transceiver 250, and a removable subscriber module 285 coupled to the controller 220.

As shown in FIG. 2, the wireless communication device 200 further includes a power management module 290, sensor module 292 and processor 294, as described in more detail below.

In one embodiment, the module 290 can reside within in the controller 220, can reside within the memory 270, can be an autonomous module, can be software, can be hardware, or can be in any other format useful for a module on a wireless communication device 200.

The display 240 can be a liquid crystal display (LCD), a light emitting diode (LED) display, a plasma display, a touch screen display or any other means for displaying information. The transceiver 250 may include a transmitter and/or a receiver. The audio input and output circuitry 230 can include a microphone, a speaker, a transducer, or any other audio input and output circuitry. The user interface 260 can include a keypad, buttons, a touch screen or pad, a joystick, an additional display, or any other device useful for providing an interface between a user and an electronic device. The memory 270 may include a random access memory, a read only memory, an optical memory or any other memory that can be coupled to a wireless communication device.

In more detail, the wireless communication device 200 shown in FIG. 2, can include: a housing 210; a controller 220 coupled to the housing 210, the controller 220 configured to control the operations of the wireless communication device and a power management module 290 configured to: sense heart rate data of a user; and configure the wireless communication device's functionality, based on the sensed heart rate data, as detailed herein. The device 200 can dramatically decrease power consumption, by providing only desired functions, on demand, based on a real time attribute of a user. Advantageously, the device 200 can provide a real-time attribute of a user, which can be used to configure the functionality of a device and conserve power.

Figure 3:
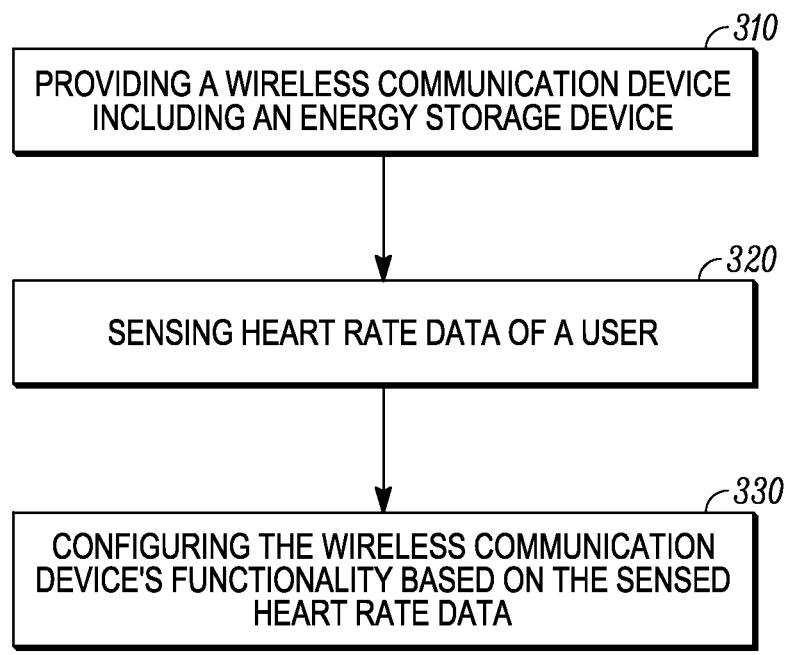
FIG. 3 is an exemplary block diagram of a wireless communication method with customizable power management according to one embodiment.

A block diagram of a wireless communication method with customizable power management 300, is shown in FIG. 3. In its simplest form, the method 300 can include: providing 310 a wireless communication device including an energy storage device; sensing 320 heart rate data of a user; and configuring 330 the wireless communication device's functionality based on the sensed heart rate data. Advantageously, the sensing step can provide heart rate data of a user, which can be used to configure the functionality of a wireless communication device and extend battery life. Advantageously, the method can provide a real-time attribute or "characteristic" of a user, which can be used to configure the functionality of a device and improve a browsing experience.

The method 300 can provide customized power management information, to conserve power.

The configuring step 330, can include controlling a user interface based on the heart rate data. For example, if the heart rate data indicates a heart rate below a certain threshold a user may want less functionality, resulting in lower power drain, and if the heart rate data indicates a heart rate above a certain threshold the user may want more functionality, as detailed below.

The method 300 can provide supplemental sensing including at least one of body temperature sensing, blood pressure sensing, glucose sensing, respiratory rate sensing, sweat sensing, moisture sensing and location sensing. Providing supplemental sensing can provide health warning information, such as location information if a warning or alarm is triggered, information for medical logging or monitoring, send alerts to a medical service center or data base, home or the like. This is discussed in greater detail, in FIG. 5.

The method 300 can display how much life the energy storage device has remaining before needing to be recharged, based on the functionality presently set. The user can utilize this information to further turn off segments or functions of the device, if desired. This feature is further detailed, in connection with FIG. 4.

The method 300 can include a prompt which can be set by a user to provide and display options to minimize power drain, at any time. Thus, a user could choose ways to minimize power drain at any time, or when a battery has reached a threshold remaining life. For example, display options can include at least one of: disabling data; enabling airplane mode; reducing display brightness; restricting application processor speed; reducing an application update rate; enabling and disabling wireless "connectivity, such as WIFI® and BLUETOOTH®; enabling and disabling location tracking". and disabling an application or segment of a device. As should be understood, other options are possible.

The sensing step 320 can include providing a first condition defining a low user activity range, a second condition defining a medium user activity range and a third condition defining a high user activity range, based on the sensed heart rate data of a user (heart rate attribute or characteristic). Thus, three ranges can be provided, for providing a low, medium and high consumption mode, based on the user's activity profile or settings, such as heart rate data. For example, the first condition can include a lower number of features and functions (ie. because a user may have just awoken or is in a normal resting heart rate condition, such as about 50-70 bpm), than the second condition (ie. when a user is moderately active or involved in low impact exercising, such as about 70-170 bpm), and the second condition can be less feature rich than the third condition, when a user is working out, for example. The third condition can be high impact exercising, such as having a heart rate of about 170-180 bpm (with a feature rich setting). Heart rate ranges can vary based on a number of factors, such as age, physical condition, weight, user history, etc. and the settings can be changed in a number of ways, as detailed herein.

In one embodiment, the first, second and third conditions, include first settable features, second settable features and third settable features, to allow a user to customize a device as desired. Thus, a user can enhance a browsing experience, by programming the device.

In one embodiment, the method 300 allows a user to program a wireless communication device to reduce power drain. For example, if a user receives a notice or prompt that there is a certain threshold time of battery life remaining, a user can turn off unneeded functions or applications, etc. This can be preset by a user or set real-time after a prompt while in use.

Thus, a user can customize his or her device in any conventional way, such as by downloading, upgrading from a site, loading from a memory stick via a USB connection and the like.

The method 300 can further include indicating that a wireless communication device is in a power conserving mode, thus indicating to a user that the device is running with a lower number of features or applications, to conserve power.

The method 300 can further include providing a notification or alarm that a predetermined sensed threshold has been met. For example, a notification or alarm can be triggered when a certain high or low threshold heart rate has been reached, blood pressure, insulin level, a certain medical condition has been triggered, and other real time user attributes are sensed. The notification can be indicated locally to a user, sent remotely to a web site or dispatcher, to a certain email address, phone number or data base, if appropriately programmed. A user's location can be indicated as well, to dispatch public safety personnel, if necessary.

The method 300 can further include providing a program which includes a heuristic algorithm that collects historical user data, so that such information can be used to configure the wireless communication device's functionality based on the collected historical user data. Thus, the device will learn a user's behavior and act appropriately, such as be on when a user is awake, be in a conservation mode when the user is asleep and provide an optimal number of applications and functions, when desired.

As previously stated, in one embodiment, the wireless communication device 200 can include: a housing 210; a controller 220 coupled to the housing 210, the controller 220 configured to control the operations of the wireless communication device and a power management module 290 configured to: sense heart rate data of a user; and configure the wireless communication device's functionality, based on the sensed heart rate data, as detailed herein. The device 200 can dramatically conserve power by providing only the desired functions or applications, on demand when needed, and as programmed.

Figure 4:
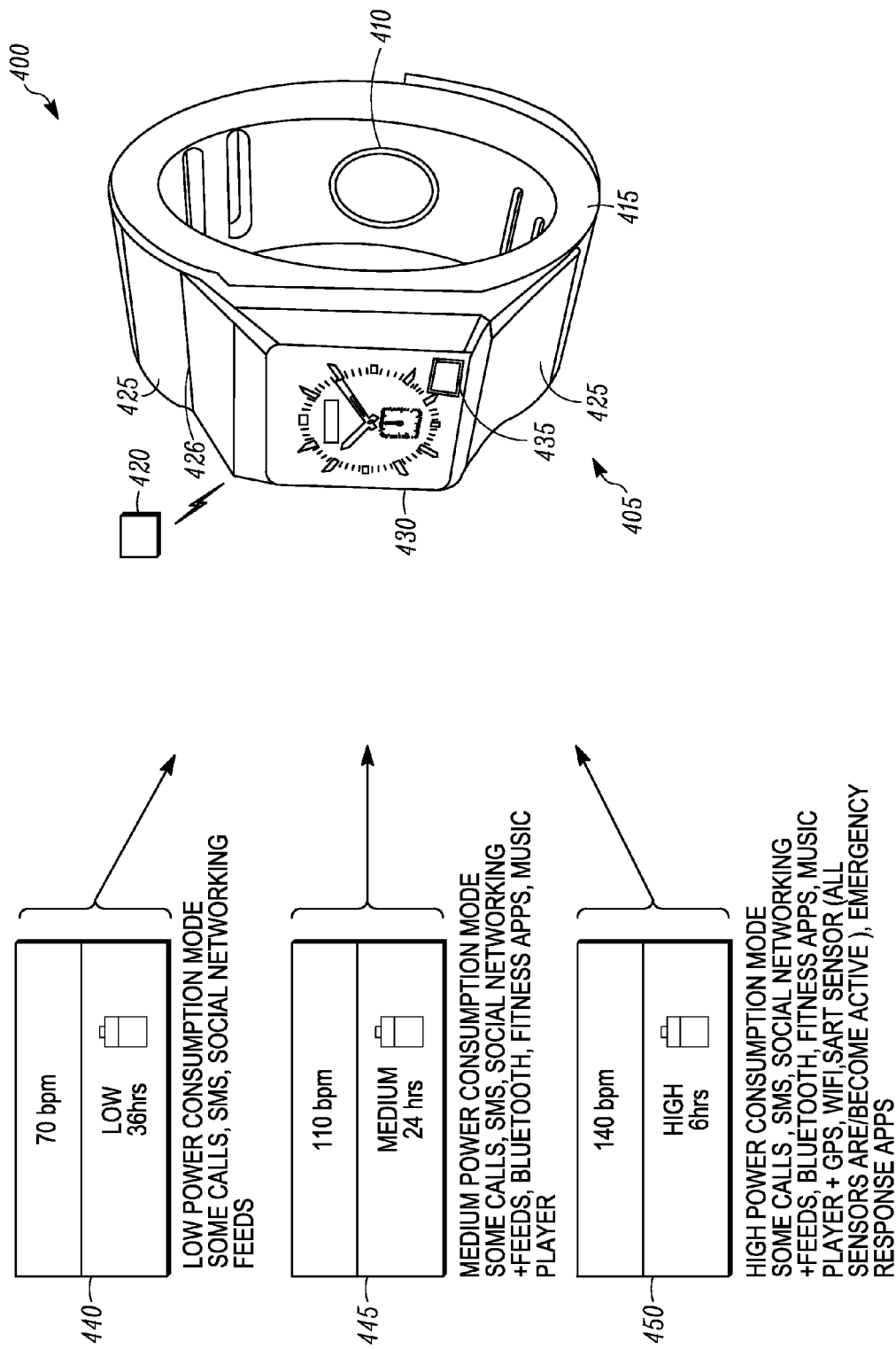
FIG. 4 is an exemplary perspective view of a wireless communication device with customizable power management according to one embodiment.

In FIG. 4, the wireless communication device 400 can be in the form of a wearable device 405, such as a wrist watch, cell phone accessory, wrist band, belt band, head band, neck band, ankle band, chest band and the like. As should be understood, other wearable devices are possible.

In a preferred embodiment, the wearable device 405 includes a heart rate sensor 410 embedded in a band 415 configured to provide heart rate data of a user and a battery 425. As should be understood, the sensor 410 can be embedded in a wrist-worn device, be a standalone accessory or integrated into a user's clothing, and can be placed any where in proximity to a user's body, such as near a heart, wrist, ankle, neck, etc. and can be directly connected or wirelessly connected to the power management module 290. The power management module 290 is configured to control a user interface to display options to minimize power drain. The power management module 290 is adapted and configured to allow a user to program the wireless communication device any time, to conserve power.

The wearable device 405 is couplable to a network 420 via a conventional method, as detailed herein. The wearable device 405 includes a housing 425 connectable with the band 415 with a connector 426, a UI display 430 with inset area 435 (in phantom), showing a low consumption mode, a medium consumption mode and a high consumption mode 440, 445 and 450, being displayed in inset 435, for example. As should be understood, wireless communication device 400 can be a cell phone, smart phone, portable computing device, wearable device alone connected to a network, or with wearable device 405 and sensors that can communicate as accessories, to monitor a user's health condition using a Personal Area Network (PAN), Body Area Network (BAN), BLUETOOTH® or WIFI®.

FIG. 4 provides three exemplary potential ranges, based on heart rate data and potentially other data or attributes:
1. Low Power Consumption Mode indicates 70 bpm. Only limited functions are provided, such as certain calls, SMS and social networking feeds. Advantageously, when a user is generally inactive, such as just waking up, so is his or her device.
2. Medium Power Consumption Mode indicates 110 bpm. More functions are "provided, such as certain calls, SMS, social networking feeds, BLUETOOTH®, fitness". applications and music player.
3. High Power Consumption Mode indicates 140 bpm. Many functions are provided, "such as calls, SMS, social networking feeds, BLUETOOTH®, fitness applications, music player and GPS, WIFI®, smart sensors (all sensors are become active), emergency". response applications. Advantageously, when a user is resting, so is the device, and when active, as in mode 2 or 3, so is his or her device.

A user can program, customize and choose additional functions and applications, to improve a browsing experience, as desired.

Referring to FIG. 5, an exemplary embodiment of a wireless communication device including a power management module 500 (similar to item 290 in FIG. 2), sensor module 505 (see item 292) and processor 530 (see item 294), as described in more detail below. The sensor module 505 can include a plurality of sensors, such as a first sensor 510, a second sensor 515, a third sensor, 520 and a fourth sensor 525. In one embodiment, the first sensor 510 is a heart rate sensor/monitor, the second sensor 515 is a temperature sensor, the third sensor 520 in a glucose sensor and the fourth sensor 525 is a blood pressure sensor. The sensors can be embedded in a common housing of a device and are coupled with the processor 530, via wired or wirelessly, as previously detailed.

The processor 530 thus receives at least a sense heart rate data of a user from the first sensor 510 and configures a device's functionality, based on the sensed heart rate data, as detailed herein. Similarly, the processor 530 can also receive temperature data, glucose data and blood pressure data from second, third and fourth sensors 515, 520 and 525. Based on some or all of this data, a device's functionality can be configured. Stated differently, based on a sensed attribute or characteristic) of a user, the functionality of a device can be configured to best serve that user and the time. The device 200 can also dramatically conserve power by providing only the desired functions, on demand when needed.

In more detail, based on the first sensor 510 data, various measures can be applied to reduce or increase the functionality of a device and reduce power consumption, as well. Here is an illustrative example:
Condition 1: Low activity zone ranging from about 50 to 70 bpm (50%-70% of maximum prescribed heart rate zone, for a certain age and condition of a user).
Conditions 2 and 3: Active activity zone ranging from about 70 to 180 bpm (70%-90% of maximum prescribed heart rate zone, for a certain age and condition of a user). Advantageously, when a user is active, so is his or her device and when a user is inactive so is the device.
Condition 4: Caution Zone at above about 180 bpm (90-100% of max HR zone) or below a threshold of about 40 bpm.

Similar measures and features can be taken or utilized for, for example, temperature, glucose, blood pressure, etc. Various notifications or alerts can be issued, and functions turned on or off, based on information of alternate sensors, for enhanced utility. The power management module 500 can: trigger certain programmed applications or functions based on a user attribute; and decrease power consumption based on a real time attribute. Thus, only desired functions are on, based on a program customized to a user's desires.

The program can be loadable and customizable by a user, by at least one of downloading a software program, adjusting a setting and inputting information in a profile, for example. Advantageously, in one use case, a user can load an application through a USB connection, for example, or download a program to load on a wireless communication device. Similarly, upgrades and customizations can be loaded in any customary way.

In a preferred embodiment, the program can include a heuristic predictive algorithm that collects, stores and aggregates historical information. In one embodiment, the processor 294 includes a program that can include predicting future user activity, based on historical information, such as user activity or usage stored in memory. The sensor module 292 can monitor real time user activity and provide a warning to the user, that based on the user activity or attribute, the energy storage device will not make it to the expected next charge. Advantageously, a user can then take appropriate measures, such as immediately recharging a battery, take power reduction action and the like.

In one embodiment, the program can include a heuristic predictive algorithm that collects and stores user activity or usage information. Correlating user activity and charge times, allows the program to learn and predict a user's typical usage and behavioral habits, based on the collected, stored and aggregated user behavior. Advantageously, this information can help a user manage the functioning of a device during a day and better manage power consumption.

In another embodiment, when a certain user activity threshold is reached or sensed by sensor module 292, a user can be alerted.

Advantageously, over time the program can provide typical use and power intelligence based on stored historical data or as programmed by a user.

The user may initially indicate a certain profile that they feel is indicative of their expected usage. This can be used by the device while history is gathered to personalize the usage predictions.

When a user is expecting to travel, it is anticipated that the device will learn of the impending trip from a calendar application, for example.

The devices 200 and 400 and methods 300 and 500 are preferably implemented on a programmed processor. However, the controllers, flowcharts, and modules may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the flowcharts shown in the figures may be used to implement the processor functions of this disclosure.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be enabled to make and use the teachings of the disclosure by simply employing the elements of the independent claims. Accordingly, the preferred embodiments of the disclosure as set forth herein are intended to be illustrative, not limiting. Various changes may be made without departing from the spirit and scope of the disclosure. In this document, relational terms such as "first," "second," and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising."

I claim:

1. A method comprising:
   sensing, by a first sensor of a wearable device, a heart rate of a user wearing the wearable device;
   determining, by a processor of the wearable device and based on the heart rate of the user, a user activity range;
   responsive to determining, by the processor of the wearable device, that the heart rate of the user indicates a low user activity range, configuring, by the wearable device, the wearable device to provide a first set of features;
   responsive to determining, by the processor of the wearable device, that the heart rate of the user indicates a medium user activity range, configuring, by the wearable device, the wearable device to provide a second set of features, wherein the second set of features is different from the first set of features; and
   responsive to determining, by the processor of the wearable device, that the heart rate of the user indicates a high user activity range, configuring, by the wearable device, the wearable device to provide a third set of features, wherein the third set of features is different from each of the first set of features and the second set of features.

2. The method of claim 1, further comprising:
   outputting, by the wearable device, a user interface configured based on whether the wearable device is currently configured to provide the first set of features, the second set of features, or the third set of features.

3. The method of claim 1, further comprising:
   sensing, by a second sensor of the wearable device, at least one of a body temperature, a blood pressure, a glucose level, a respiratory rate, a sweat level, a moisture level or location of the user; and
   determining, by the processor of the wearable device, based at least in part on the heart rate of the user and the at least one of the body temperature, the blood pressure, the glucose level, the respiratory rate, the sweat level, the moisture level, or the location, whether to configure the wearable device with one of the first set of features, the second set of features, or the third set of features.

4. The method of claim 1, further comprising outputting, by a display of the wearable device, an amount of time remaining before the wearable device needs to be recharged.

5. The method of claim 1, further comprising outputting, by a display of the wearable device, a graphical user interface including options to minimize power drain including at least one of: disabling data, enabling airplane mode, reducing display brightness, restricting application processor speed, disabling an application, enabling and disabling wireless connectivity, enabling and disabling location tracking, disabling segments of a wireless communication device, or reducing an application update rate.

6. The method of claim 1, wherein the first set of features includes fewer features than the second set of features and the second set of features includes fewer features than the third set of features.

7. The method of claim 1, wherein the first set of features includes first user configurable features, the second set of features includes second user configurable features and the third set of features includes third user configurable features.

8. The method of claim 1, further comprising outputting, by a display of the wearable device, an indication that the wearable device is operating in a power conserving mode.

9. The method of claim 1, further comprising configuring, by the processor of the wearable device, based on historical user data, functionality of the wearable device.

10. The method of claim 9, further comprising:
predicting, by the processor of the wearable device, based on the historical user data, a future activity of the user; and
configuring, by the processor of the wearable device, based on the future activity of the user, the wearable device to provide one of the first set of features, the second set of features, or the third set of features.

11. A wearable device, comprising:
a housing;
a controller coupled to the housing, the controller configured to control the operations of the wearable device;
a heart rate sensor coupled to the housing, the heart rate sensor configured to sense a heart rate of a user wearing the wearable device; and
a power management module configured to:
determine, based on the heart rate of the user, a user activity range;
responsive to determining that the heart rate of the user indicates a low user activity range, configure the wearable device to provide a first set of features;
responsive to determining that the heart rate of the user indicates a medium user activity range, configure the wearable device to provide a second set of features, wherein the second set of features is different from the first set of features; and
responsive to determining that the heart rate of the user indicates a high user activity range, configure the wearable device to provide a third set of features, wherein the third set of features is different from each of the first set of features and the second set of features.

12. The wearable device of claim 11, further comprising:
a display configured to display a graphical user interface including options to minimize power drain including at least one of: disabling data, enabling airplane mode, reducing display brightness, restricting application processor speed, disabling an application, enabling and disabling wireless connectivity, enabling and disabling location tracking, disabling segments of a wireless communication device, or reducing an application update rate.

13. The wearable device of claim 11, further comprising:
a display configured to display a graphical user interface configured based on whether the wearable device is currently configured to provide the first set of features, the second set of features, or the third set of features.

14. The wearable device of claim 11, further comprising:
a sensor module configured to sense at least one of a body temperature, a blood pressure, a glucose level, a respiratory rate, a sweat level, a moisture level or location of the user,
wherein the power management module is configured to determine, based at least in part on the heart rate of the user and the at least one of the body temperature, the blood pressure, the glucose level, the respiratory rate, the sweat level, the moisture level, or the location, whether to configure the wearable device with one of the first set of features, the second set of features, or the third set of features.

15. The wearable device of claim 11, wherein the power management module is further configured to configure, based on historical user data, functionality of the wearable device.

16. The wearable device of claim 15, wherein the power management module is further configured to:
predict, based on the historical user data, a future activity of the user; and
configure, based on the future activity of the user, the wearable device to provide one of the first set of features, the second set of features, or the third set of features.

* * * * *